United States Patent
Erickson et al.

(10) Patent No.: US 7,341,576 B2
(45) Date of Patent: *Mar. 11, 2008

(54) MEDICAL DELIVERY/EXTRACTION SYSTEM

(75) Inventors: Dean A. Erickson, Greenfield, WI (US); Christopher J. Groppi, Franklin, WI (US)

(73) Assignee: Bioform Medical, Inc., San Mateo, CA (US)

( * ) Notice: Subject to any disclaimer, the term of this patent is extended or adjusted under 35 U.S.C. 154(b) by 292 days.

This patent is subject to a terminal disclaimer.

(21) Appl. No.: 10/779,132

(22) Filed: Feb. 13, 2004

(65) Prior Publication Data

US 2004/0220530 A1     Nov. 4, 2004

Related U.S. Application Data

(63) Continuation-in-part of application No. 10/197,453, filed on Jul. 17, 2002, which is a continuation-in-part of application No. 10/113,680, filed on Mar. 29, 2002.

(51) Int. Cl.
*A61M 5/31* (2006.01)
(52) U.S. Cl. .................................... 604/240
(58) Field of Classification Search ............... 604/189, 604/241, 110, 263, 187, 240
See application file for complete search history.

(56) References Cited

U.S. PATENT DOCUMENTS

| | | | |
|---|---|---|---|
| 387,454 A | 8/1888 | Siegenthaler | |
| 3,391,694 A | 7/1968 | Spaeth | 128/218 |
| 3,450,135 A | 6/1969 | Sarnoff | 128/221 |
| 3,628,524 A | 12/1971 | Jamshidi | 128/2 B |
| 3,630,192 A | 12/1971 | Jamshidi | 128/2 B |
| 3,662,457 A | 5/1972 | Gores | 29/508 |
| 3,670,727 A * | 6/1972 | Reiterman | 604/177 |
| 4,233,974 A | 11/1980 | Desecki et al. | 128/215 |
| 4,237,882 A * | 12/1980 | Wickham | 604/192 |
| 4,256,119 A | 3/1981 | Gauthier | 128/754 |
| 4,266,555 A | 5/1981 | Jamshidi | 128/753 |
| 4,340,066 A | 7/1982 | Shah | 128/749 |
| 4,396,021 A | 8/1983 | Baumgartner | 128/754 |
| 4,403,617 A | 9/1983 | Tretinyak | 128/754 |
| 4,430,080 A | 2/1984 | Pasquini et al. | 604/240 |
| 4,445,893 A * | 5/1984 | Bodicky | 604/165.04 |
| 4,518,383 A | 5/1985 | Evans | 604/51 |
| 4,573,978 A | 3/1986 | Reilly | 604/240 |
| 4,609,370 A | 9/1986 | Morrison | 604/165 |
| 4,642,103 A | 2/1987 | Gettig | 604/234 |
| 4,655,226 A | 4/1987 | Lee | 128/754 |
| 4,667,684 A | 5/1987 | Leigh | 128/754 |
| 4,668,226 A | 5/1987 | Omata et al. | 604/272 |

(Continued)

*Primary Examiner*—Kevin C. Sirmons
*Assistant Examiner*—Catherine N. Witczak
(74) *Attorney, Agent, or Firm*—Foley & Lardner LLP

(57) ABSTRACT

A medical delivery or extraction system comprising a needle assembly having a needle and a hub coupled to the needle. The hub includes a verification region or component. A syringe body rotatably coupled to the needle assembly includes at least one indicia on the outer surface thereof. When the indicia corresponds to the verification region, the user is provided with an indication that the syringe body is properly connected to the needle assembly. The system also includes a lever arm coupled to the needle assembly. The lever arm is sized and positioned to provide a user with a mechanism of easily securing the needle assembly to the syringe without the use of external tools.

17 Claims, 7 Drawing Sheets

U.S. PATENT DOCUMENTS

| | | |
|---|---|---|
| 4,758,218 A | 7/1988 | Kiefer et al. .................. 604/53 |
| 4,799,495 A | 1/1989 | Hawkins et al. ............ 128/754 |
| 4,838,282 A | 6/1989 | Strasser et al. ............. 128/754 |
| 4,842,592 A | 6/1989 | Caggiani et al. ............ 604/283 |
| 4,844,087 A | 7/1989 | Garg ......................... 128/753 |
| 4,846,804 A | 7/1989 | Davis et al. ................. 604/164 |
| 4,881,551 A | 11/1989 | Taylor ........................ 128/754 |
| 4,889,529 A | 12/1989 | Haindl ....................... 604/274 |
| 4,923,447 A | 5/1990 | Morgan ...................... 604/198 |
| 4,967,762 A | 11/1990 | DeVries ..................... 128/753 |
| 5,005,585 A | 4/1991 | Mazza ........................ 128/754 |
| 5,026,355 A | 6/1991 | Sweeney et al. ............ 604/243 |
| 5,031,634 A | 7/1991 | Simon ........................ 128/753 |
| 5,059,186 A | 10/1991 | Yamamoto et al. ......... 604/280 |
| 5,061,251 A | 10/1991 | Juhasz ........................ 604/198 |
| 5,078,690 A | 1/1992 | Ryan .......................... 604/187 |
| 5,081,997 A | 1/1992 | Bosley, Jr. et al. ..... 128/662.02 |
| 5,205,833 A | 4/1993 | Harsh et al. ................. 604/240 |
| 5,226,898 A | 7/1993 | Gross ......................... 604/243 |
| 5,242,405 A | 9/1993 | Howe ......................... 604/125 |
| 5,328,466 A | 7/1994 | Demark ...................... 604/93 |
| 5,336,191 A | 8/1994 | Davis et al. ................. 604/165 |
| 5,385,561 A | 1/1995 | Cerny ........................ 604/264 |
| 5,716,346 A | 2/1998 | Farris ......................... 604/243 |
| 5,782,505 A | 7/1998 | Brooks et al. .............. 285/175 |
| 5,833,674 A | 11/1998 | Turnbull et al. ............ 604/283 |
| 5,860,955 A | 1/1999 | Wright et al. ................ 604/99 |
| 5,941,853 A | 8/1999 | Collins ....................... 604/165 |
| 6,063,057 A | 5/2000 | Choh .......................... 604/99 |
| 6,132,402 A | 10/2000 | Tessmann et al. .......... 604/240 |
| 6,167,886 B1 | 1/2001 | Engel et al. ................ 128/885 |
| 6,210,372 B1 | 4/2001 | Tessmann et al. .......... 604/181 |
| 6,280,430 B1 | 8/2001 | Neftel et al. ................ 604/411 |
| 6,565,550 B1* | 5/2003 | Klein et al. ................. 604/506 |
| 6,966,897 B2* | 11/2005 | Shimazaki ................... 604/189 |
| 2003/0187409 A1* | 10/2003 | Erickson ..................... 604/240 |
| 2003/0187410 A1* | 10/2003 | Erickson ..................... 604/240 |
| 2005/0049560 A1* | 3/2005 | Hauri ......................... 604/263 |

* cited by examiner

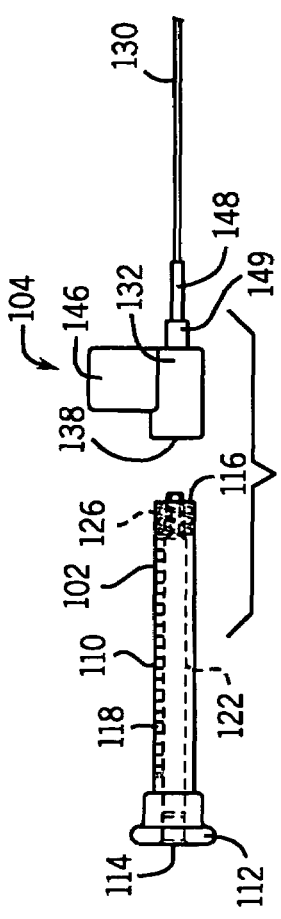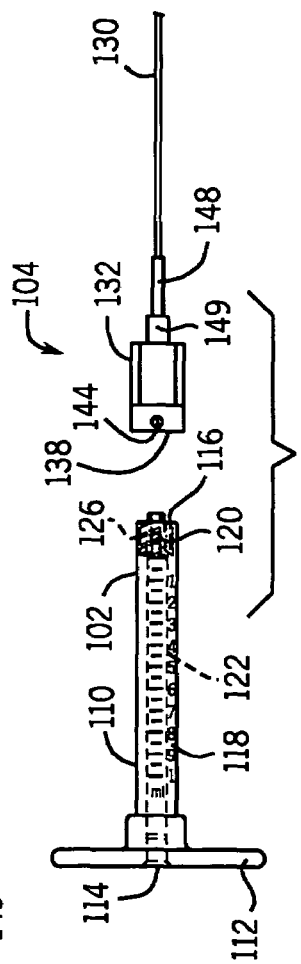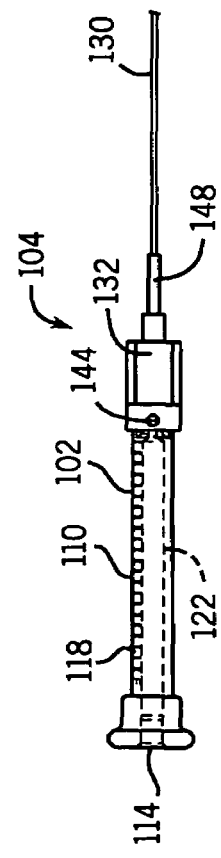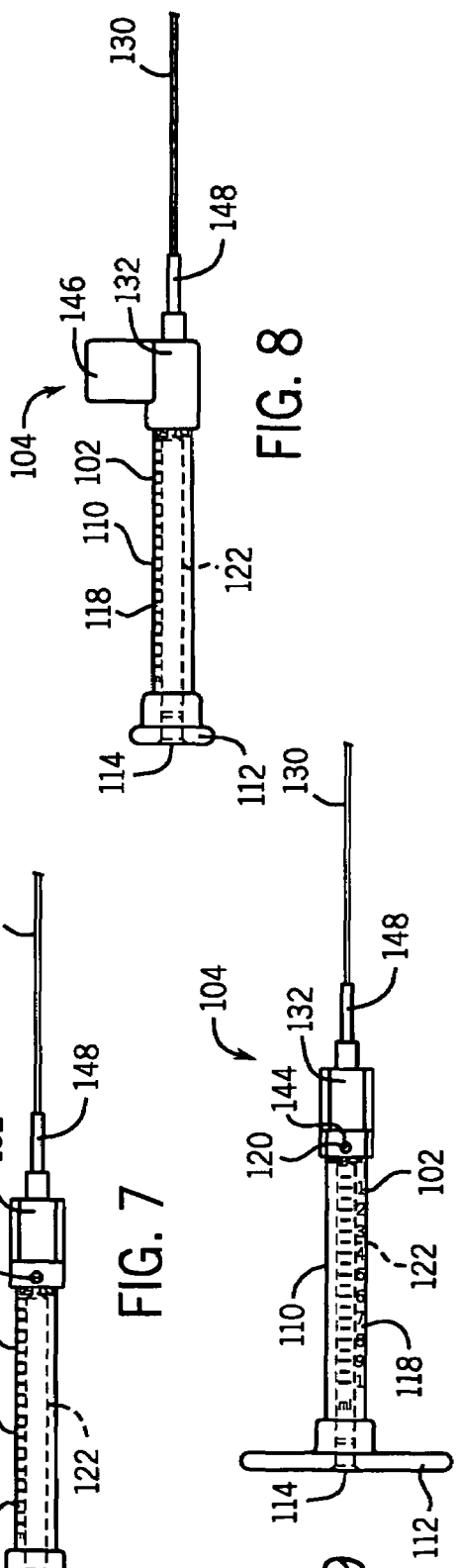

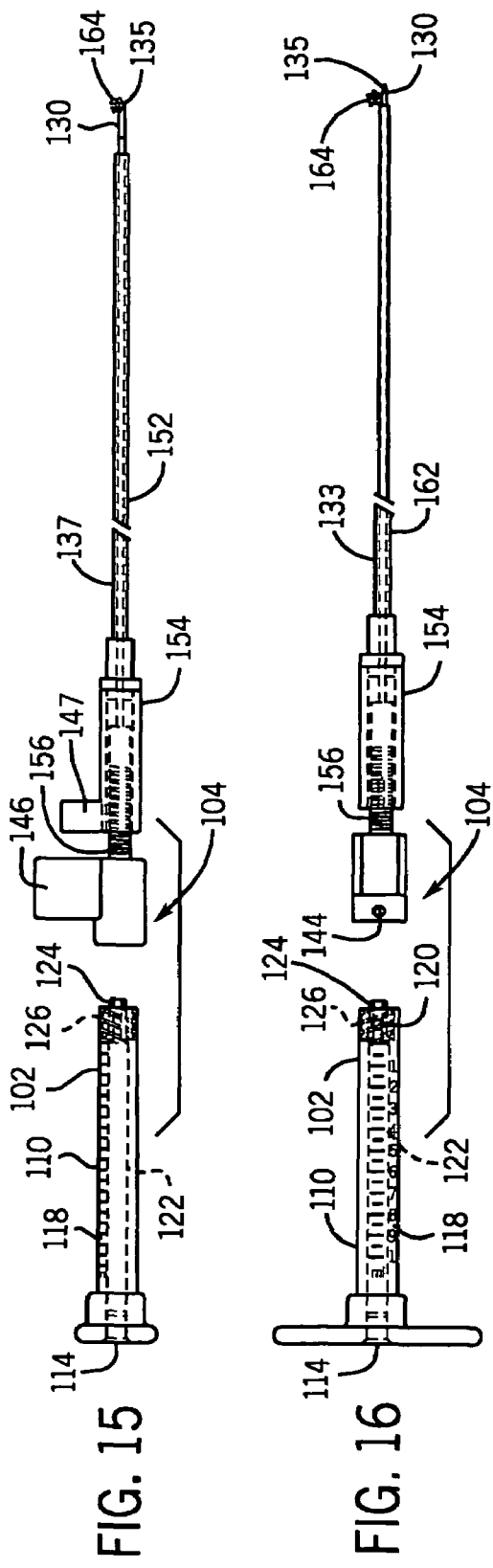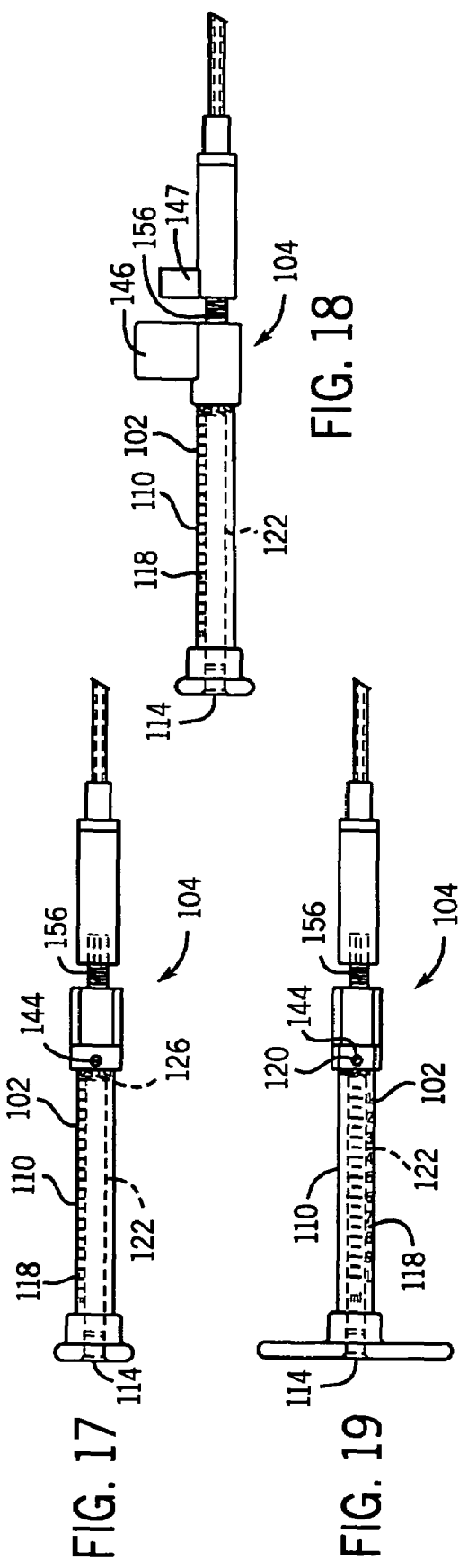

MEDICAL DELIVERY/EXTRACTION SYSTEM

CROSS-REFERENCE TO RELATED PATENT APPLICATIONS

This application is a continuation-in-part of U.S. patent application Ser. No. 10/197,453, filed Jul. 17, 2002, which is a continuation-in-part of U.S. patent application Ser. No. 10/113,680, filed Mar. 29, 2002.

FIELD OF THE INVENTION

The present invention is directed to a medical delivery/extraction system. More particularly, the present invention is related to a medical delivery/extraction system with a lever arm to easily and fully tighten a needle to the syringe.

BACKGROUND OF THE INVENTION

Syringe and needle assemblies have been used for a number of years for the purpose of injecting fluids into or withdrawing fluids from a body. These fluids may include medicine, blood or other types of biological materials. Due to the multitude of infectious diseases which may be carried by bodily fluids such as blood, it is extremely important that any potential leakage of fluid during an injection or withdrawal process be kept to an absolute minimum.

One location in a delivery/extraction system where bodily fluids and/or other substances may leak from the system is the connection area between the syringe and the needle assembly. Because syringes and needle assemblies are often marketed and/or manufactured separately, a doctor, nurse or other technician is required to properly connect the needle assembly to the syringe. If the needle assembly is not properly connected to the syringe, the possibility of a poor connection and accidental leakage of biological materials increases significantly. This correspondingly increases the risk of exposure to hazardous materials.

The type of fluid or other biological media being delivered to or from the syringe may also contain materials, components, or ingredients (hereinafter, "material") that can separate at a poor connection when exposed to the injection pressures developed in the syringe. The material separation can cause further problems of injecting or extracting the full contents of the syringe through the needle. A needle assembly properly connected to the syringe would significantly reduce the possibility of material, component, or ingredient separation from occurring.

A variety of mechanisms have been developed to securely fasten needle assemblies to syringes, but each have their drawbacks. For example, a number of conventional mechanisms include a linear connection between the syringe and the needle assembly in the form of a track or groove, in which the needle assembly slides onto the syringe. Systems with linear connections often include o-ring type seals that are located a certain distance from the path of the fluid material. This distance between the seal and the material pathway may cause delivery and/or extraction problems for certain types of materials. Other types of conventional systems involve a rotational fitting between the needle assembly and the syringe. These systems allow for a line-to-line seal that is integral to the material path, but the systems are somewhat limited in their ability to indicate to the user when an adequate or proper connection has been achieved. Furthermore, some of these systems may be prone to being "overtightened" which can affect the functionality and/or safety of the completed assembly. Also, it often can be difficult to determine whether the needle assembly is properly connected to the syringe. In whichever case, an improperly made connection between the needle assembly and the syringe can have hazardous results and/or functional/operational problems.

Additionally, most conventional injection needles do not provide a mechanism for adequately tightening the needle to a standard luer syringe without the use of tools by the user. A few products currently available provide a double grip design in order to produce an increased leverage, but double grip designs typically expect that the user will rotate the needle relative to the syringe. Tightening the needle relative to syringe can cause additional tissue trauma if the needle is in the tissue. Some designs also do not permit for the repeated connection and disconnection of the needle with different syringes, as the needle's plastic luer threads tend to distort or wear under the required tightening force. Furthermore, some delivery and extraction systems do not provide a sufficiently tight seal between the syringe and needle luer connections or a connection that clears particles from the luer surface of the syringe.

Finally, conventional injection needles do not provide a mechanism by which to adequately tighten the needle to a standard luer syringe using the sheath assembly. Having such ability would help to prevent needle stick injuries through the placement of the handle on an axis that is offset from the needle tip.

SUMMARY OF THE INVENTION

It is therefore an object of the invention to provide an improved delivery or extraction system that provides a simple mechanism for ensuring a proper connection between components.

It is another object of the invention to provide an improved delivery or extraction system that includes a mechanism to indicate to a user that a proper connection has been achieved.

It is still another object of the invention to provide an improved delivery or extraction system that minimizes the incidence of fluids or other bio-material escaping from the system.

It is yet another object of the present invention to provide an improved delivery and extraction system that provides a visual indication of whether an adequate or proper connection has been made in the system.

It is another object of the present invention to provide an improved delivery and extraction system that is simple to use while still maintaining a high degree of safety.

It is another object of the invention to provide an improved delivery or injection system which provides a high degree of leverage when tightening the needle onto a syringe.

It is yet another object of the invention to provide an improved delivery and extraction system that permits sufficient tightening of the system without the use of external tools.

It is still another object of the invention to provide an improved delivery and extraction system that allows for the repeated connection and disconnection of the needle with different syringes.

It is another object of the present invention to provide an indicator means that provides accurate and concurrent positioning of both linear and angular orientation, ensuring indication of a proper connection.

It is also an object of the invention to provide an improved delivery and extraction system that allows a user to assemble a needle to a syringe using a sheath assembly.

In accordance with the above objects, a medical delivery and extraction system is provided. The system comprises, among other things, a needle assembly including a needle with a hub formed therein, the hub containing a lever arm. A syringe body is rotatably coupled to the needle assembly. The syringe body includes at least one indicia on a portion of the body, and the needle hub includes a verification region on a portion thereof. The indicia and verification region are arranged on the syringe body and needle hub, respectively, such that when the syringe body is properly fastened to the needle assembly, the indicia aligns with the verification region, giving the user an indication that the needle assembly is properly connected to the syringe body. The lever arm provides the user a high degree of leverage when tightening the needle onto the syringe without necessitating the use of external tools.

BRIEF DESCRIPTION OF THE DRAWINGS

The foregoing advantages and features of the invention will become apparent upon reference to the following detailed description and the accompanying drawings, of which:

FIG. 5 is a side view of a needle assembly and syringe before being fastened;

FIG. 6 is a side view rotated ninety degrees about the longitudinal axis of the needle assembly and syringe of FIG. 5;

FIG. 7 is a side view of the needle assembly rotated ninety degrees and syringe of FIG. 5 as the needle assembly is partially fastened to the syringe;

FIG. 8 is a side view of the needle assembly and syringe of FIG. 5 as the needle assembly is properly connected to the syringe;

FIG. 9 is a side view rotated ninety degrees of the needle assembly and syringe of FIG. 8 as the needle assembly is properly connected to the syringe;

FIG. 15 is a side view of an unfastened medical delivery system including a protective sheath;

FIG. 16 is a side view rotated ninety degrees about the longitudinal axis of an unfastened medical delivery/extraction system including a cannula;

FIG. 17 is a side view of the needle assembly rotated ninety degrees and syringe of the medical delivery system of FIG. 15 during the securing process;

FIG. 18 is a side view of the medical delivery system of FIG. 15 when properly connected;

FIG. 19 is a side view rotated ninety degrees about the longitudinal axis of the medical delivery system of FIG. 18 when properly connected;

DETAILED DESCRIPTION OF THE INVENTION

Figure 1:
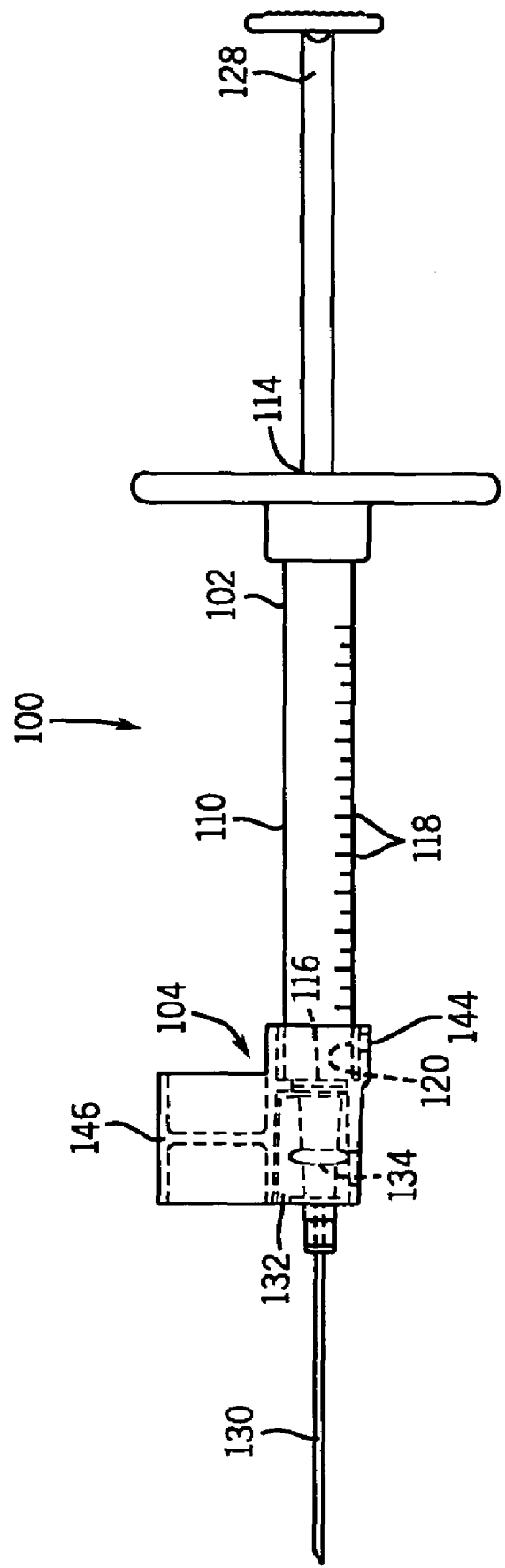
FIG. 1 is a side view of a medical delivery system according to one embodiment of the invention.
Figure 2:
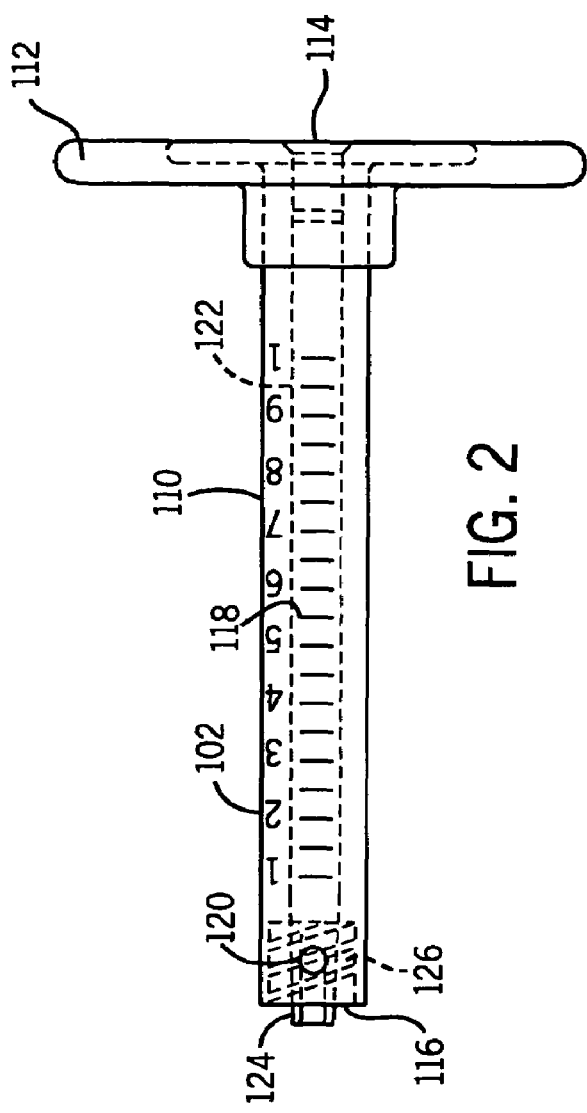
FIG. 2 is a detailed side view of a syringe according to one embodiment of the present invention.

A medical delivery or extraction system is shown generally at 100 in FIGS. 1-4. The medical delivery or extraction system 100 comprises a syringe 102 and a needle assembly 104. The syringe 102 comprises a syringe body 110 coupled to an end-piece 112 (best seen in FIG. 2). The syringe body 110 includes a plunger receiving end 114 and a needle assembly receiving end 116. The plunger receiving end 114 is open such that it may accept a plunger 128 that is used to force fluid into or out of the syringe 102. The syringe body 110 also includes a plurality of volume indicia 118 for measuring the amount of fluid inside the syringe 102 at any given moment.

The syringe 102 also includes an inner body 122 (shown in phantom in FIG. 2) on the inside of the syringe 102. The inner body 122 comprises a passageway through which the fluid primarily flows. The inner body 122 terminates at a connection portion 124. In the area around the connection portion 124, there are a plurality of threads 126 (shown in phantom) formed on the inside of the syringe body 110.

An indicator mark 120 is also included at the needle assembly receiving end 116 of the syringe 102. The indicator mark 120 is used to determine whether the syringe 102 is properly connected to the needle assembly 104. The indicator mark 120 may take a variety of forms. In a preferred embodiment of the invention, the indicator mark 120 comprises a colored dot which is visible by a user. The indicator mark 120 can take a variety of other forms, however, including lines, figures, numbers, colored bands, etc. and a variety of conventional indicating methods including aligning lines or figures, compression rings, etc. Additionally, it is also possible for the indicator mark 120 simply to be a color opposite that of the surrounding portion of the syringe body 110 or to be reverse printed from that described in this embodiment. Furthermore, it is possible to have multiple color bands or other mechanisms for indicating varying degrees of making the connection. The indicator mark 120 is preferably imprinted on the outer surface of the syringe body 110 or imbedded inside the syringe body 110. Furthermore, the indicator mark 120 can comprise a depression, ridge, or groove which mates with the needle assembly 104.

Figure 4:
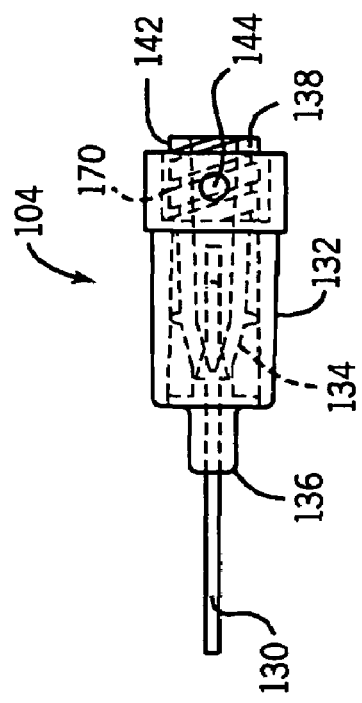
FIG. 4 is a detailed side view of a portion of the needle assembly of FIG. 3 rotated ninety degrees about its central longitudinal axis.
Figure 3:
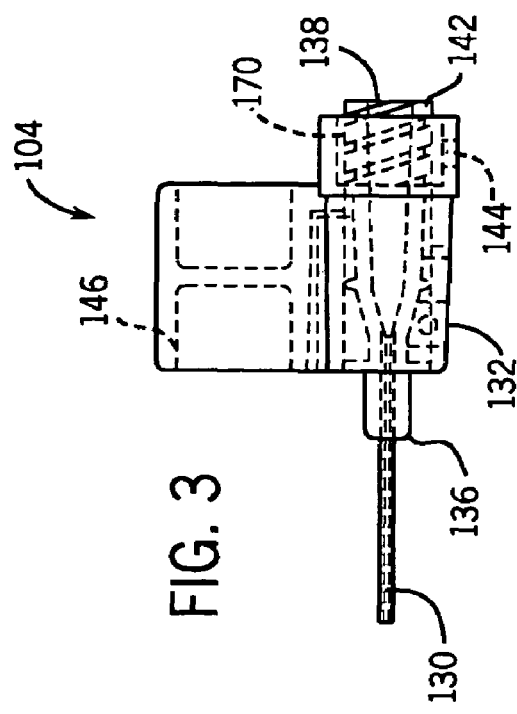
FIG. 3 is a detailed side view of a needle assembly for mating with the syringe of FIG. 2.

The needle assembly 104 comprises a needle 130 (shown partially in phantom and full line in FIGS. 3 and 4) coupled to a luer connection 132. The luer connection 132 includes a hub 134 (shown in phantom) formed on the inside thereof. The hub 134 is hollow and runs from a first end 136 to a second end 138. The hub 134 is sized to accept the needle 130 in a snug relationship. The hub 134, in one embodiment of the invention, also includes a hub ridge 142 at the second end 138. Alternatively, the hub 134 may include a plurality of hub threads 170, shown best in FIGS. 10-14. As shown in FIGS. 3 and 4, the hub ridge 142 and/or the hub threads 170 are used to mate the needle assembly 104 with the syringe 102 shown in FIGS. 1 and 2. The luer connection 132 also includes a lever arm 146. The lever arm 146 is used to fasten and unfasten the needle assembly 104 from the syringe 102.

The luer connection 132 also includes a viewing region 144. In a preferred embodiment of the invention, the viewing region 144 comprises a circular opening. It is also possible for the viewing region 144 to comprise a transparent material. The viewing region 144 is used to determine if the needle assembly 104 is properly connected to the syringe 102. As is explained herein, when the indicator mark 120 of the syringe 102 is clearly visible through the viewing region 144, then it is understood that the syringe 102 is properly connected to the needle assembly 104.

Figure 10:
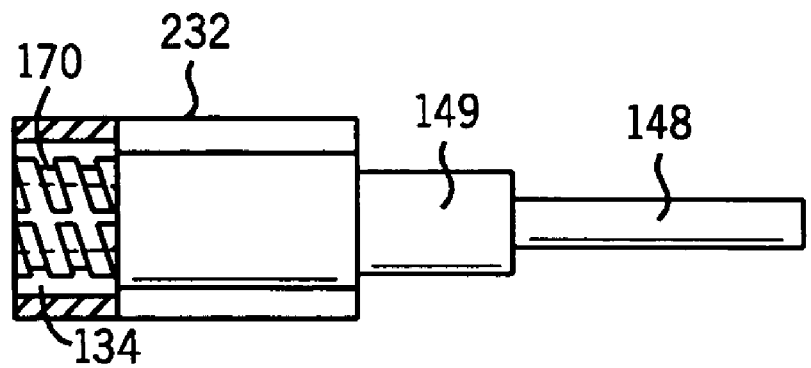
FIG. 10 is a side view of a luer connection according to another embodiment of the invention.
Figure 11:
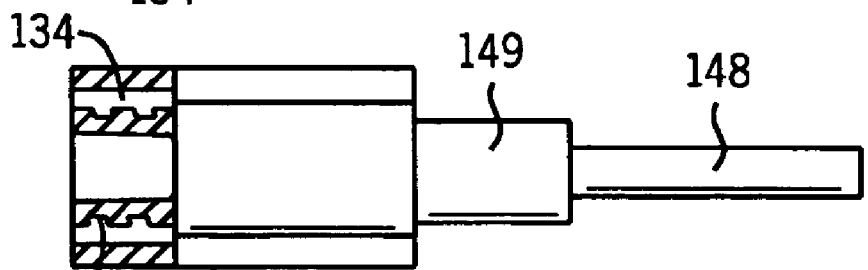
FIG. 11 is another side view of the luer connection of FIG. 10.
Figure 12:
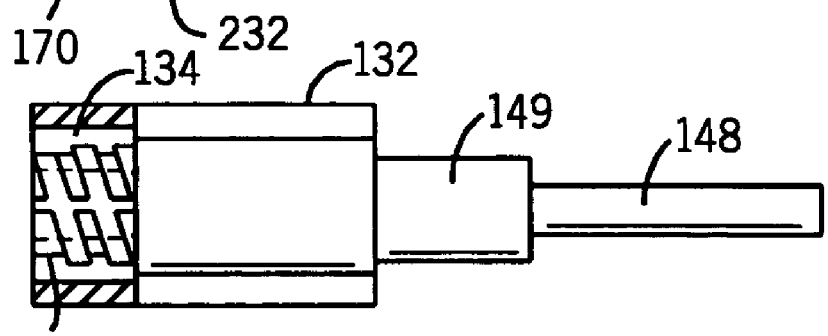
FIG. 12 is a side view of a modified luer connection according to still another embodiment of the invention.
Figure 13:
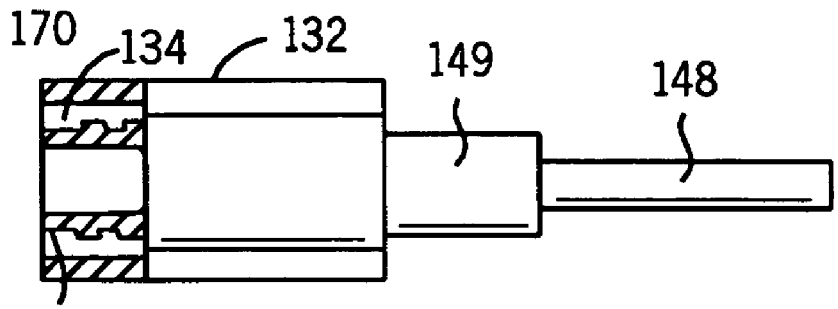
FIG. 13 is a side view of a modified luer connection according to yet another embodiment of the invention.
Figure 14:
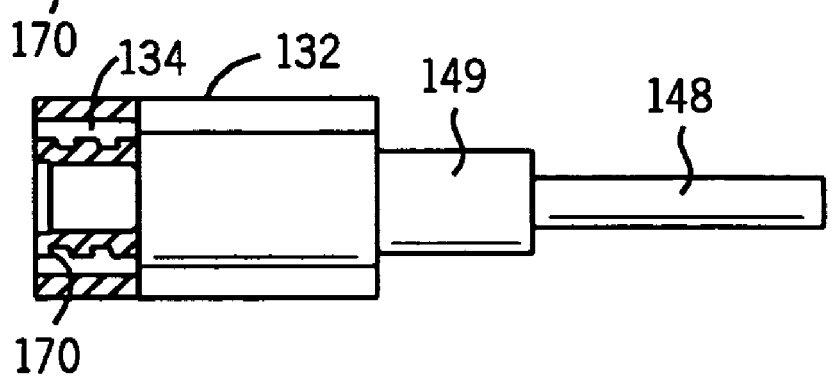
FIG. 14 is a side view of a modified luer connection according to still another embodiment of the invention.
Figure 20A:
FIG. 20A is an alternate embodiment of the invention in which a beveled needle is connected to a tightening lever arm's luer fitting, and a cannula is connected to a linearly adjustable member with the needle in a retracted position.
Figure 20B:
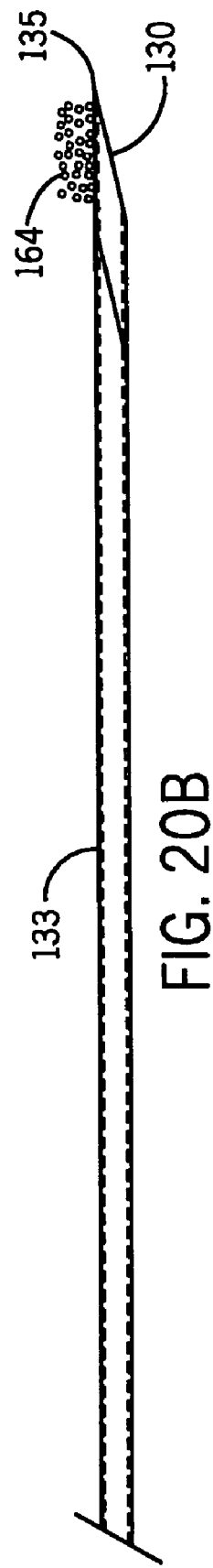
FIG. 20B shows the needle of FIG. 20A with the needle in an open and injection position.
Figure 21A:
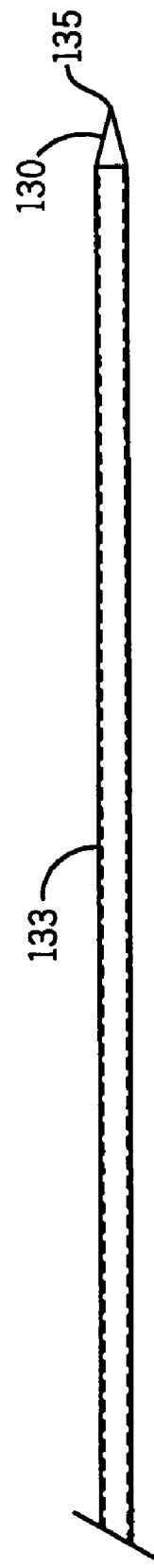
FIG. 21A is an alternate embodiment of the invention in which a pointed needle is connected to a tightening lever arm's luer fitting, and a cannula is connected to a linearly adjustable member with the needle in a retracted position.
Figure 21B:
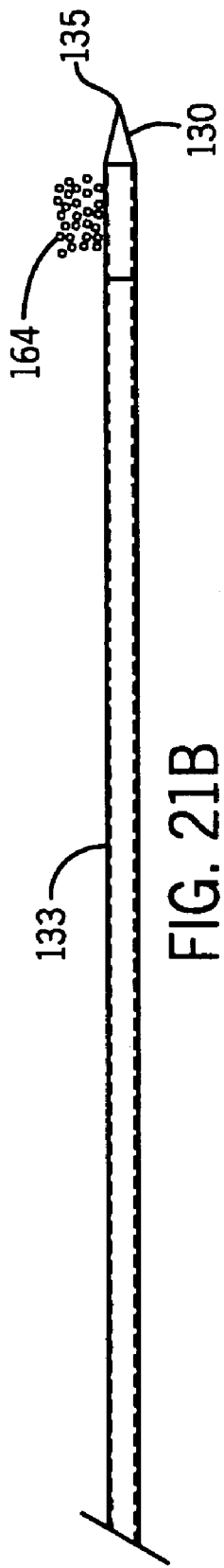
FIG. 21B shows the needle of FIG. 21A with the needle in an open and injection position.

FIGS. 10-14 show various example types of threaded sealing connections that may be incorporated into the present invention. FIGS. 10 and 11 show a standard threaded luer connection 232, including a strain relief portion 148 and a luer end 170. FIGS. 12-14 disclose modified luer connections 132, including a modified luer connection 132 with the initial leading threads removed, (see FIG. 12); a modified luer connection 132 with the initial leading thread removed, while the inner diameter begins straight at a diameter smaller than the standard luer 232 and tapers to a normal luer diameter (see FIG. 13); and a modified luer connection 132 in which the initial diameter does not taper nor chamfer fully to the second diameter, but incorporates a ninety degree or less angled step between the two diameters to help push particulates off of the luer taper surface (see FIG. 14). A variety of types of connections could also be used, as would be understood by one of ordinary skill in the art.

Depending upon the nature and type of threads 126, the number of indicator marks 120 on the syringe body 110 may also vary. For example, if a single lead thread is used, only one of the indicator marks 120 is required on the syringe body 110. If a double lead thread is used, however, two of the indicator marks 120 should be incorporated onto the syringe body 110, each being approximately 180° from the other. In this case, the medical delivery or extraction system 100 would be properly connected when either of the indicator marks 120 is aligned with the viewing region 144. If a triple lead thread is used, three indicator marks 120 would be used with each of the indicator marks 120 being approximately 120° from the other indicator marks 120. In general, the number of the indicator marks 120 needed would correlate to the number of thread leads used.

The operation of the medical delivery or extraction system 100 is generally as follows. As shown in FIGS. 5 and 6, the needle assembly 104 is separable from the syringe 102. If the user desires to couple the needle assembly 104 to the syringe 102, the user brings the second end 138 of the luer connection 132 towards the needle assembly receiving end 116 of the syringe body 110. When the second end 138 of the luer connection 132 comes into contact with the needle assembly receiving end 116 of the syringe body 110, the user either twists the lever arm 146 of the luer connection 132 or grips the lever arm 146 of the luer connection 132 and twists the syringe body 110. The mating action of the threads 126 with the hub threads 170 (see FIG. 4) causes the luer connection 132 to couple to the syringe body 110. As is shown in FIGS. 7-9, the connection between the luer connection 132 and the syringe body 110 becomes more pronounced as the luer connection 132 is twisted relative to the syringe body 110. As is shown in FIG. 8, when the luer connection 132 is only partially upon the syringe body 110, the indicator mark 120 is not yet shown or visible through the viewing region 144. As the user continues to twist the luer connection 132, the indicator mark 120 ultimately aligns with the viewing region 144, as best shown in FIG. 9. At this position a proper connection has been achieved between the needle assembly 104 and the syringe 102, and the user is given an indication that additional tightening is not necessary. The user is then able to perform the particular procedure using the medical delivery or extraction system 100. When the user desires to remove the needle assembly 104 from the syringe 102, the user simply rotates the luer connection 132 in the opposite direction using the lever arm 146.

The delivery or extraction system 100 of the present invention can be used in virtually any situation that requires an indication and assurance of a proper connection for rotationally connected medical delivery or extraction devices. Such environments range from sterile hospital suites to non-sterile doctors' offices. The system 100 could be used at ambient conditions in addition to hot or below freezing conditions and dry or humid conditions. The system 100 can also be packaged and sterilized using conventionally known methods and can be provided and used for non-sterile applications. The individual components can all be manufactured using conventionally known techniques resulting in a relatively low cost.

As mentioned previously, a variety of indicia can be used for indicating that the syringe 102 is properly connected to the needle assembly 104. For example, a variety of visual indicators could be used, and it is also possible to have an audible indication of a proper connection. This can be accomplished using a form of snap fitting in a mechanical design, an electronic computer chip in an electrical design, or other design systems. A combination of visual and audio indications could also be used. Furthermore, a number of the individual components can be replaced and/or modified depending upon the particular needs. For example, the syringe 102 could be in the form of a container such as a cartridge, vial or bottle, while the needle assembly 104 could be replaced with a different type of mechanism or device. Different types of seal interfaces, such as tapered seals, face seals, etc., could be used to ensure a secure connection, and connections other than luer connections could be used. For example, a variety of types of threads or a twist locking mechanism could be incorporated into the system 100.

The present invention also provides for an extended, single torque lever arm 146. The lever arm 146 can be used for many applications where a delivery or extraction system 100 including a needle 130 is used and requires a very tight seal, such as during the delivery of particle laden and/or high viscosity materials. The lever arm 146 provides a mechanism for adequately tightening the needle assembly 104 to a standard syringe luer fitting by an operator without the need for ancillary tools or other assistance. The lever arm 146 provides the operator with greater leverage and reduced hand force for tightening and, by virtue of the increased tightness, a greater seal pressure. The lever arm 146 therefore allows for the easier connection and disconnection of the needle assembly 104 to the syringe. The lever arm 146 also provides a comfortable grasp for the user.

The lever arm design is sized to provide an easy grip point between the user's thumb and finger to encourage holding the needle assembly 104 steady while twisting the syringe 102 onto the needle assembly 104. Conventional designs such as double wing, no wing, and short single arm designs encourage the user to hold the syringe 102 and twist the needle assembly 104 onto the syringe 102. The design of the present invention discourages this practice, providing a distinct advantage for procedures in which the needle 130 is required to be left in place and not twisted while the syringe 102 is removed and/or attached and while the syringe 102 or component exchanges occur at the luer connection 132.

For a single torque form of the lever arm 146, the needle assembly 104 is connected to the mating syringe 102 by holding the lever arm 146 and rotating the syringe 102 onto the needle assembly 104 until a tight connection has been made. The lever arm 146 provides significant leverage for the operator, reducing the force normally required to tighten the needle assembly 104. Removal of the syringe 102 is achieved by simply holding the injection needle torque lever arm 146 and rotating the syringe 102 in the opposite direction as when tightened. A syringe change-out occurs by removing an existing form of the syringe 102 and connecting a new form of the syringe 102 as detailed previously.

The extraction or delivery system 100 according to the present invention may also include an adjustable outer sheath 137 that covers the needle 130 and needle tip 135 or cannula 133 that tapers and/or blends into the needle tip 135 during part of the injection procedure. Examples of these embodiments are shown in FIGS. 15, 16, 20A-B and 21A-B. The delivery or extraction system 100 may also include a modified luer design that provides a means of wiping the mating luer's outer diameter surface while the parts are being connected together.

Types of styles which may be used include a modified full thread luer connection 132 that has a straight and smaller than normal lead-in diameter, shown in FIG. 13 or a standard luer lead-in diameter which quickly changes to a long, continuous diameter that is approximately equal to the smallest luer diameter, shown in FIG. 14. These modified styles provide the needle 130 a means of the pushing material located on the syringe luer sealing surface off that surface. The designs promote a proper and tight seal between the sealing surfaces of the luer fittings without the injection material being trapped or sandwiched between, preventing a tight seal from forming. These designs could include a modified full luer thread that has some of the lead-in threads removed (as shown in FIG. 13). This feature combined with the other modifications described herein would further allow the leading edge of the needle luer to grip snuggly around the smallest diameter of the mating syringe luer and distort or flare outward as the needle assembly 104 is tightened fully onto the luer fitting. The material of construction is pliable and flexible to allow distortion of the lead-in diameter.

FIGS. 15-16, 20A-2B and 21A-21B show that the invention may include a controlled mechanism for adjusting and locking-in-place a sheath 137 or cannula 133, placed over a needle 130, while the needle 130 remains in position. In this particular embodiment, the outer sheath 137 or the cannula 133 is connected to a linearly adjustable member 154 which is integral and connected to the tightening lever arm's 146 luer fitting. The needle 130 could be replaced with a stylet while still allowing use of the system in a manner similar to that described or allowing removal of the stylet altogether once placed in its desired location.

In one embodiment of the invention and as shown in FIG. 15, the needle 130 is connected to the tightening lever arm's 146 luer fitting and the protective sheath 137 is connected to the linearly adjustable member. In a second embodiment and as shown in FIGS. 16, 21A, 21B, 22A and 22B, the beveled or pointed needle 130 is connected to the tightening lever arm's 146 luer fitting, and the cannula 133 is connected to the linearly adjustable member. In this particular embodiment of the invention, a preferred form of the needle 130 is a side discharge needle that has a solid metal point. With this design, the needle opening 164 is initially covered by the outer cannula 133, thus acting as a stylet when first introduced into the body. Once in place, the cannula 133 is retracted by use of the linear adjustable member, and the needle opening 164 is exposed. The needle tip 135 remains in the original injection position as the cannula 133 is retracted. After injection, the cannula 133 can be slid back over the exposed needle opening 164 and the entire needle assembly 104 withdrawn from the site. This alternative design is preferred over standard and non-coring needles for applications where the needle 130 must puncture through tough membranes such as cartilage or scar tissues, as standard and non-coring needles can core when pushed through these tissues.

One method of sheath or cannula adjustment is shown in the FIGS. 15-19 where a multi-slotted arm on the tightening lever arm 146 end mates with a correspondingly tabbed adjustment member 147 that can be rotated about ninety degrees to lock into place. This design allows for secure multiple position adjustment of the outer sheath 137 or cannula 133 with respect to the inner needle 130. A second adjustment method comprises a channeled (and optionally detented) arm on the tightening lever arm end that mates with a corresponding tab and tightening screw or optional plunger (not shown) on the adjustment member 147. This design permits secure multiple position adjustment of the outer sheath 137 or the cannula 133 without requiring rotation of one member with respect to the other.

The addition of a modified luer connection 132 does not change the connection and removal methods for the needle 130, but simply adds a wiping element on the needle luer fitting as shown in FIGS. 13 and 14. The wiping element presses immediately against the smallest diameter of the syringe luer connection 124 and expands against the mating luer's taper as the luer fittings are drawn together and the connection tightened. Removal of the needle assembly 104 allows its luer fitting to return to its normal shape while ensuring the syringe's luer surface is wiped of any debris or particulate matter.

An integrated adjustment member may also be used to provide a controlled mechanism for adjusting and locking-in-place the sheath 137 or the cannula 133 placed over the needle or stylet 130 while the needle or stylet 130 remains in position. In one embodiment of the invention and as shown in FIG. 15, a sheathed form of the needle 130 is connected to the syringe. The needle's sheath 137 is slid over the needle tip 135, and the covered needle assembly 104 is inserted. Once the needle sheath 137 protrudes out of the scope, the sheath 137 is retracted and the needle 130 placed into the tissue location desired. Upon completion of the procedure, the needle 130 is removed from the injection site, the sheath 137 pushed over the needle tip 135, and the entire needle assembly 104 is pulled out of the scope. The sheath 137 allows the needle 130 to be placed through a scope with no damage to the scope channel.

In an alternative embodiment of the invention and as shown in FIG. 16, the adjustable cannula 133 is connected to the syringe 102, and the cannula 133 is slid over the needle tip 135 to cover and seal the needle opening 164 of the side discharge needle 130. The needle 130 is placed into the tissue location desired, and the cannula 133 is retracted. The injection occurs and the entire needle assembly 104 is pulled out of the injection site. The cannula 133 is slid over the needle opening 164 again, and the needle 130 placed into another tissue location. The cannula 133 is again retracted and a new injection occurs. The process is repeated until all injections desired are completed. The sliding cannula 133 allows penetration into tough or fibrous tissue that may core a regular needle 130 during its penetration.

The present invention can be used in conjunction with virtually any environment and procedure which requires assurance of a tight connection using only the operator's hand strength. Environments ranging from sterile hospital suites to non-sterile offices primarily at ambient conditions are acceptable, although the invention may be used in environments ranging from hot and humid conditions to dry and below freezing conditions. The types of materials used may range from 100% plastic to 100% metal, or a combination of the two materials. An elastomeric compound could also be added and used for the sealing and/or wiping applications.

The lever arm 146 for the invention can be molded using standard injection molding and insert molding techniques. Differences in the shape, size, and/or profile of the lever arm 146 can also be made to further ergonomically enhance the lever arm's 146 characteristics. Additionally, the lever arm 146 or other components of the injection needle 130 could be color coded to an industry standard, indicating the needle gauge of the product. The plastic tubing used can be manufactured from readily available extruded tubing known to those in the art. The needles 130 and respective cannulas 133 can be produced by current extrusion and fabrication methods such as grinding, drilling, cutting, milling, and polishing. The assembly of the extraction or delivery system 100 can be completed with standard assembly, forming, bonding, printing, and molding operations. The system can be packaged and sterilized using currently available methods, with Ethylene Oxide (EtO) being the preferred sterilization method.

Figure 22:
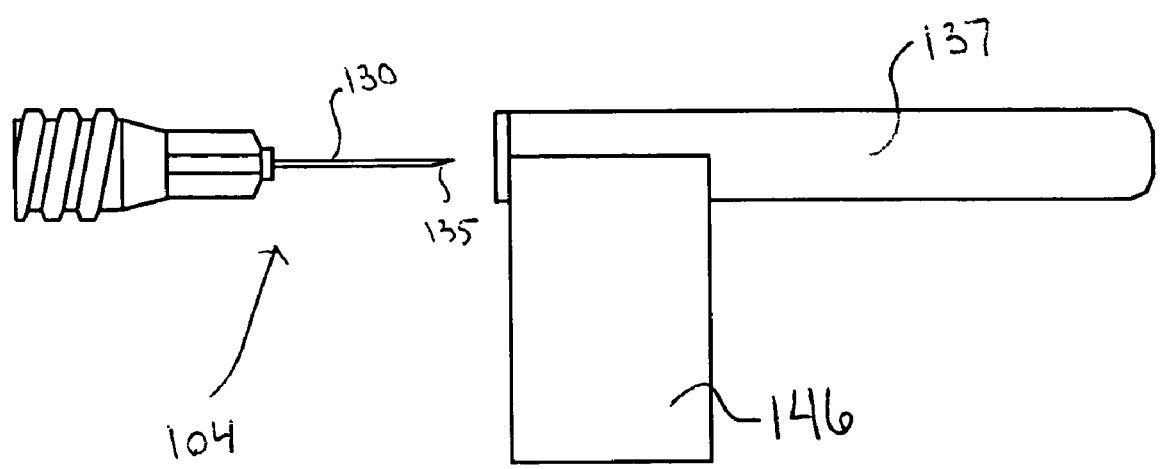
FIG. 22 shows an alternate embodiment of the invention in which the positioning handle is located on the needle sheath, with the needle sheath operatively and removably engaging the needle.

Another embodiment of the invention as shown and described in FIG. 22. FIG. 22 shows the sheath 137 as including the handle or lever arm 146. In this configuration, the sheath 137 removably connects to the needle assembly 104, and the lever arm 146 is used to position the needle 130. In addition, this configuration also provides for a handling location for the sheath 137 that is offset from the axis of the needle 130.

It should be understood that the above description of the invention and specific examples and embodiments, while indicating the preferred embodiments of the present invention, are given by demonstration and not limitation. For example, although a luer type thread is discussed in detail, the invention can easily be used with any device that uses a "twist-to-tighten" connection (i.e. devices that use threads, ¼ turn connections, etc.) Many changes and modifications within the scope of the present invention may therefore be made without departing from the spirit thereof and the present invention includes all such changes and modifications.

What is claimed is:

1. An injection or extraction system, comprising:
    a syringe having a body with a connection joint at first end thereof and at least one assembly indicator mark proximate thereto and having a central longitudinal axis;
    a needle assembly, comprising a luer connection and a needle partially disposable therein, with a channel therethrough; and
    the luer connection comprising a hub formed therein, the hub having a first end for engaging the needle and a second end for mating with the connection joint of the syringe, the first end of the syringe body at least partially disposable within the luer connection and a hollow sheath assembly operatively and removably connected to the needle assembly, the sheath assembly including a lever arm attached thereto, the needle assembly insertable therein,
    the needle movable parallel to the longitudinal axis and rotationally fixed about the longitudinal axis in relation to the sheath,
    a viewing region positioned in the luer connection of the needle assembly and positionable over the first end of the syringe for viewing at least one of the assembly indicator mark indicating whether the needle assembly is securely fastened to the syringe; and
    wherein the sheath is rotatable about the longitudinal axis by actuation of the lever arm, rotation of the sheath also rotating the needle to secure the needle assembly to the syringe without the use of external tools.

2. The injection or extraction system of claim 1, wherein the lever arm extends such that a portion of the lever arm is asymmetrically positioned offset from longitudinal axis.

3. The injection or extraction system of claim 1, wherein the lever arm includes a needle gauge indication for the injection or extraction system.

4. The injection or extraction system of claim 3, wherein the indication comprises a color coding indicative of a particular needle gauge.

5. The injection or extraction system of claim 1, wherein the at least one assembly indicator mark comprises at least one indicia on the outer surface of the syringe body, the indicia corresponding to a verification component denoting when the syringe is properly connected to the needle assembly.

6. The injection or extraction system of claim 5, wherein the indicia snap fits with the verification component when the syringe is properly connected to the needle assembly.

7. The injection or extraction system of claim 5, wherein the indicia comprises a colored indicator.

8. The injection or extraction system of claim 5, wherein the syringe includes a double lead thread for mating with the hub of the needle assembly, and wherein the at least one assembly indicator mark comprises first and second indicia positioned on the outer surface of the syringe body such that the syringe body is rotatably and properly connected to the needle assembly when the verification component corresponds to either the first indicia or the second indicia.

9. The injection or extraction system of claim 5, wherein the syringe includes a triple lead thread for mating with the hub of the needle assembly, and wherein the at least one assembly indicator mark comprises first, second and third indicia positioned on the outer surface of the syringe body such that the syringe body is rotatably and properly connected to the needle assembly when the verification component corresponds to one of the first, second or third indicia.

10. The injection or extraction system of claim 1, wherein the syringe includes a thread on an inner surface of the hub for mating with a ridge on the hub.

11. The system of claim 10, wherein the syringe includes a luer fitting on the inside thereof, the luer fitting mating with the hub.

12. A medical delivery system, comprising:
a syringe having a body with a connection joint at a first end thereof and at least one assembly indicator mark proximate thereto;
a needle assembly, comprising a needle and a luer connection, rotatably and removably coupled to the connection joint; and
a hollow sheath assembly removably coupled to the needle assembly, the sheath and needle moveable independently along a longitudinal axis of the needle and coupled for rotation about the longitudinal axis;
the hollow sheath assembly including a sheath handle positioned asymmetrically with respect to the longitudinal axis of the needle to permit a user to secure the needle assembly to the syringe via rotational movement of the sheath and the coupled needle without the use of external tools; and
a viewing region positioned in the luer connection of the needle assembly and positionable over the first end of the syringe for viewing at least one of the assembly indicator mark indicating whether the needle assembly is securely fastened to the syringe.

13. The medical delivery system of claim 12, further comprising audible means for indicating whether the needle assembly is securely fastened to the syringe.

14. The medical delivery system of claim 13, further comprising means for visually indicating the needle gauge, the indicating means operatively connected to the needle assembly.

15. The injection or extraction system of claim 12, wherein the at least one assembly indicator mark comprises at least one indicia on the outer surface of the syringe body, the indicia corresponding to a verification component denoting when the syringe is properly connected to the needle assembly.

16. The injection or extraction system of claim 15, wherein the indicia snap fits with the verification component when the syringe is properly connected to the needle assembly.

17. The injection or extraction system of claim 15, wherein the indicia comprises a colored indicator.

* * * * *